US006953568B1

(12) United States Patent
Esmon et al.

(10) Patent No.: US 6,953,568 B1
(45) Date of Patent: Oct. 11, 2005

(54) TARGETING OF MOLECULES TO LARGE VESSEL ENDOTHELIUM USING EPCR

(75) Inventors: Charles T. Esmon, Oklahoma City, OK (US); Jun Xu, Oklahoma City, OK (US)

(73) Assignee: Oklahoma Medical Research Foundation, Oklahoma City, OK (US)

( * ) Notice: Subject to any disclaimer, the term of this patent is extended or adjusted under 35 U.S.C. 154(b) by 0 days.

(21) Appl. No.: 09/139,425

(22) Filed: Aug. 25, 1998

(51) Int. Cl.$^7$ ................... A61K 49/00; A61K 39/40; A61K 38/00; A61K 31/70; C12N 15/63
(52) U.S. Cl. ............... 424/9.2; 424/178.1; 424/179.1; 424/181.1; 424/183.1; 435/69.1; 435/320.1; 435/325; 435/455; 514/2; 514/44
(58) Field of Search ................... 424/178.1, 9.2, 424/179.1, 181.1, 183.1; 435/4, 6, 69.1, 320.1, 435/325, 455; 514/2, 44; 536/23.1

(56) References Cited

U.S. PATENT DOCUMENTS

| | | | |
|---|---|---|---|
| 3,625,214 A | 12/1971 | Higuchi | 424/424 |
| 4,244,946 A | 1/1981 | Rivier et al. | 514/15 |
| 4,305,872 A | 12/1981 | Johnston et al. | 530/330 |
| 4,316,891 A | 2/1982 | Guilleman et al. | 514/11 |
| 4,629,784 A | 12/1986 | Stammer | 530/328 |
| 4,782,137 A | 11/1988 | Hopp et al. | 530/328 |
| 4,789,734 A | 12/1988 | Pierschbacher | 530/395 |
| 4,792,525 A | 12/1988 | Ruoslahti et al. | 435/402 |
| 4,906,474 A | 3/1990 | Langer et al. | 514/772.3 |
| 4,925,673 A | 5/1990 | Steiner et al. | 424/455 |
| 4,980,286 A | 12/1990 | Morgan et al. | 435/371 |
| 5,009,889 A | 4/1991 | Taylor et al. | 424/94.64 |
| 5,136,916 A | 8/1992 | Shibukawa | 84/627 |
| 5,202,253 A * | 4/1993 | Esmon et al. | 435/240.27 |
| 5,225,537 A * | 7/1993 | Foster | 530/380 |
| 5,254,532 A * | 10/1993 | Schwarz et al. | 514/2 |
| 5,298,599 A | 3/1994 | Rezaie et al. | 530/350 |
| 5,571,786 A * | 11/1996 | Eibl et al. | 514/8 |
| 5,695,993 A * | 12/1997 | Fukudome et al. | 435/325 |
| 5,698,189 A | 12/1997 | Rowe et al. | 424/78.08 |
| 5,749,968 A | 5/1998 | Melanson et al. | 118/300 |
| 5,779,673 A | 7/1998 | Roth et al. | 604/101 |
| 5,804,392 A | 9/1998 | Esmon et al. | 435/7.1 |
| 5,847,085 A * | 12/1998 | Esmon et al. | 530/381 |
| 5,852,171 A * | 12/1998 | Fukudome et al. | 530/350 |
| 6,399,064 B1 * | 6/2002 | Fukudome et al. | |

FOREIGN PATENT DOCUMENTS

| | | |
|---|---|---|
| EP | 0 318 201 A2 | 5/1989 |
| EP | 0 687 687 A2 | 12/1995 |
| WO | WO 89/02747 A1 | 4/1989 |
| WO | WO 90/08556 A1 | 8/1990 |
| WO | WO96/05303 * | 2/1996 ................. 435/325 |
| WO | WO 96/05303 | 2/1996 |
| WO | WO 96/20732 | 7/1996 |
| WO | WO 96/21470 | 7/1996 |
| WO | WO 98/20041 | 5/1998 |
| WO | WO 98/55142 A1 | 12/1998 |
| WO | WO 99/00673 A1 | 1/1999 |

OTHER PUBLICATIONS

Jans et al. Nuclear targeting by growth factors, cytokines, and their receptors: a role in signalling? Bioessays Vo.. 21(5):400-411, May 26, 1998.*
Rosenkranz et al. Receptor-mediated endocytosis and nuclear transport of a transfecting DNA construct. Experimental Cell Research. vol. 199:323-329, May 1992.*
Delporte et al. Triplex-Forming oligonucleotides can modulate aquaporin-5 gene expression in epithelial cells. Antisense & Nucleic Acid Drug Development. vol. 7:523-539, May 1997.*
Michaud et al. Most nuclear proteins are imported by a single pathway. Experimental Cell Research vol. 208:128-136, Mar. 1993.*
Antisense '97: A roundtable on the state of the industry. Nature Biotechnology. vol. 15:519-524, Jun. 15, 1997.*
Rojanasakul, Y. Antisense oligonucleotide therapeutics: drug delivery and targeting. Advanced Drug Delivery Reviews. vol. 18:115-131, Jan. 1996.*

(Continued)

Primary Examiner—Sumesh Kaushal
(74) Attorney, Agent, or Firm—Fulbright & Jaworski (57) ABSTRACT

Endothelial protein C receptor (EPCR) is found primarily on endothelial cells of large vessels. EPCR translocates from the plasma membrane surface to the nucleus. Molecules which bind to EPCR can be carried from the plasma membrane surface to the nucleus. These molecules include antibodies to EPCR and activated protein C. Protein C, which also binds to EPCR, can be internalized by endothelial cells, but does not enter the nucleus. Thus, EPCR translocation from the plasma membrane to the nucleus provides a means of delivering nucleic acid such as DNA, proteins such as transcription factors, diagnostic agents or other types of drugs to the nucleus of endothelial cells, particularly those on large blood vessels. Conjugates of the materials to be delivered to the nucleus can be formed by ionic or covalent coupling. For example, proteins, including fusion proteins, can be directly conjugated to an anti-EPCR monoclonal antibody. Covalent attachment of positively charged polymers, such as polylysine, to an anti-EPCR antibody allows nucleic acid to bind by ionic charges. Steptavidin and biotin can also be used to conjugate molecules to anti-EPCR antibodies. These conjugated antibodies are transported to the nucleus by EPCR. Eamples demonstrate selective transport to the nucleus which is mediated by EPCR. Molecules transported include activated protein C, antibodies to EPCR, and steptavidin-biotin conjugates. Modification of anti-EPCR monoclonal antibodies by covalently coupling to polylysine allows binding of an expression vector to the modified antibody and translocation to the nucleus.

21 Claims, 2 Drawing Sheets

OTHER PUBLICATIONS

Anderson, W. F. Human Gene Therapy. Nature vol. 392:25-30, Apr. 30, 1998.*

Verma et al. Gene therapy-promises, problems and prospects. Nature vol. 389:239-242, Sep. 18, 1997.*

Orkin et al. Report and recommendations of the panel to assess the NIH investment in research on gene therapy, Dec. 7, 1995.*

Rosenberg et al, Gene Therapist, Heal Thyself. SCIENCE 287:1751, 2000.*

Touchette, Gene Therapy: Not ready for prime time. Nat. Med. 2(1) 7-8, 1996.*

Fukudome et al, Activation mechanism of anticoagulant protein C in large blood vessels involving the endothelial cell protein C receptor.J Exp Med. 6;187(7):1029-35, 1998.*

Stearns-Kurosawa et al The endothelial cell protein C receptor. Cell surface expression and direct ligand binding by the soluble receptor(PNAS 93:10212-10216, 1996).*

Abe, et al., "Granulocyte proteases and hydrogen peroxide synergistically inactive thrombomodulin of endothelial cells in vitro," *J. Lab. Clin. Med.* 123(6):874-881, (1994).

ACCP/SCCM Consensus Conference, "Definitions for Spesis and Organ Failure and Guidelines for the Use of Innovative Therapies in Sepsis," *Chest* 101(6):1644-1655 (1992).

Agrawal, et al., "Oligodeoxynucleoside phosphoramidates and phosphorothioates as inhibitors of human immunodeficiency virus," *Proc. Natl. Acad. Sci. USA* 85(19): 7079-7083 (1988).

Arend, et al., "Building of IL-1α, IL-1β, and IL-1 Receptor Antagonist by Soluble IL-1 Receptors and Levels of Soluble IL-1 Receptors in Synovial Fluids," *J. Immunol.* 153:4766-4774 (1994).

Asakura, et al. "Plasma Levels of Soluble Thrombomodulin Increase in Cases of Disseminated Intravascular Coagulation With Organ Failure," *Am. J. Hematol.* 38:281-287 (1991).

Askew, B., et al., "Molecular Recognition with Convergent Functional Groups, 6, Synthetic and Structural Studies with a Model Receptor for Nucleic Acid Components", *J. Am. Chem. Soc.*, 111:1082-1090 (1989).

Bangalore, et al., "High affinity binding sites for activated protein C and protein C on cultured human umbilical vein endothelial cells. Independent of protein S and distinct from known ligands," *Thromb Haemos* 72(3):465-74 (1994).

Berg, et al., "Aberrant RNA splicing of the protein C and protein S genes in health individuals," *Blood Coag Fibrinol.* 7:625-631 (1996).

Blume, et al., "Triple helix formation by purine-rich oligonucleotides targeted to the human dihydrofolate reductase promoter," *Nucleic Acids Res.* 20(7):1777-84 (1992).

Bock, P. E. "Active Site Selective Labeling of Serine Proteases with Spectroscopic Probes Using Thioester Peptide Chloromethyl Ketones: Demonstration of Thrombin Labeling Using $N^\alpha$-[(Acetylthio)acetyl]-D-Phe-Pro-Arg-$CH_2Cl$," *Biochemistry* 27:6633-6639 (1988).

Boehme, et al., "Release of thrombomodulin from endothelial cells by concentrated action of TNF-α and neutrophils: in vivo and in vitro studies," *Immunology* 87:134-140 (1996).

Bourin and Lindahl, "Review Article: Glycosaminoglycans and the regulation of blood coagulation," *Biochem. J.* 289: 313-330 (1993).

Clackson, et al., "Making antibody fragments using phage display libraries," *Nature* 352:624-688 (1991).

Conway and Rosenberg, "Tumor Necrosis Factor Suppresses Transcription of the Thrombomodulin Gene in Endothelial Cells," *Mol. Cell. Biol.* 8(12):5588-5592 (1988).

Cooney, et al., "Site-specific oligonucleotide binding represses transcription of the human c-myc gene in vitro," *Science.* 241(4864):456-9 (1988).

Crooke, et al., "Progress toward oligonucleotide therapeutics: pharmacodynamic properties," *FASEB J.* 7(6): 533-9 (1993).

Curtis, et al. "IL-1 and its receptor are translocated to the nucleus," *J. Immunol.* 144:1295-1303 (1990).

Dahlbäck, "Inhibition of Protein $C_B$ Cofactor Function of Human and Bovine Protein S by C4b-binding Protein," *J. Biol. Chem.* 261(26):12022-12027 (1986).

Dahlbäck, "Protein S and C4b-Binding Protein: Components Involved in the Regulation of the Protein C Anticoagulant System," *Thromb. Haemostas.* 66:49-61 (1991).

Daugherty, et al., "Polymerase chain reaction facilitates the cloning, CDR-grafting, and rapid expression of a murine monoclonal antibody directed against the CD18 component of leukocyte integrins," *Nucl. Acids Res.* 19(9):2471-2476 (1991).

Dittman and Majerus, "Structure and Function of Thrombomodulin: A Natural Anticoagulant," *Blood* 75(2): 329-336 (1990).

Dittman, W. A. "Thrombomodulin—Biology and Potential Cardiovascular Applications," *Trends Cardiovasc. Med.* 1 (8):331-336 (1991).

Dreyfus et al., "Treatment of Homozygous Protein C Deficiency and Neonatal Purpura Fulminans with a Purified Protein C Concentrate," *N. Engl. J. Med.* 325(22):1565-1568 (1991).

Duval-Valentin, et al., "Specific inhibition of transcription by triple helix-forming oligonucleotides," *Proc Natl Acad Sci U S A.* 89(2):504-8 (1992).

Ecke, et al., "Possible identity of kallikrein binding protein with protein C inhibitor," *Agents Actions Suppl.* 38 ( Pt 1):182-9 (1992).

Edgell, et al., "Permanent cell line expressing human factor VIII-related antigen established by hybridization," *Proc. Natl. Acad. Sci.* (*USA*) 80:3734-3737 (1983).

Engelman et al., "Identifying Nonpolar Transbilayer Helices in Amino Acid Sequences of Membrane Proteins," *Annu. Rev. Biophys. Chem.* 15:321-53 (1986).

Esmon and Owen, "Identification of an endothelial cell cofactor for thrombin-catalyzed activation of protein C," *Proc. Natl. Acad. Sci.* (*USA*) 78(4):2249-2252 (1981).

Esmon and Schwarz, "An Update on Clinical and Basic Aspects of the Protein C Anticoagulant Pathway," *Trends Cardiovasc. Med.* 5(4):141-148 (1995).

Esmon, "Factors regulating the inhibition of thrombin by antithrombin III," in *Chemistry and Biology of Thrombin*, R. L. Lundblad, J. W. Fenton, II, and K. G. Mann, editors. Ann Arbor Science, Ann Arbor., 403-411 (1977).

Esmon, "Protein S and Protein C—Biochemistry, Physiology, and Clinical Manifestation of Deficiencies," *Trends Cardiovasc. Med.* 2(6):214-220 (1992).

Esmon, "The Roles of Protein C and Thrombomodulin in the Regulation of Blood Coagulation," *J. Biol. Chem.* 264(9): 4743-4746 (1989).

Esmon, et al., "Complex Formation Between Thrombin Thrombomodulin Inhibits Both Thrombin-catalyzed Fibrin Formation and Factor V Activation," *J. Biol. Chem.* 2257 (14):7944-7947 (1982).

Esmon, et al., "Protein C Activation," *Methods Enzymol.* 222:359-385 (1993).

Fukudome and Esmon, "Identification, Cloning, and Regulation of a Novel Endothelial Cell Protein C/Activated Protein C Receptor," *J. Biol. Chem.* 269(42):26486-26491 (1994).

Fukudome and Esmon, "Molecular Cloning and Expression of Murine and Bovine Endothelial Cell Protein C/Activated Protein C Receptor (EPCR)—The Structural and Functional Conservation in Human, Bovine and Murine EPCR*,"*J. Biol. Chem.* 270(10):5571-5577 (1995).

Fukudome, et al., "Identification, Cloning, and Regulation of a Novel Endothelial Cell Protein C/Activated Protein C Receptor," *Circulation* 90(4):I133 (1994).

Galvin, et al., "Reconstitution of Rabbit Thrombomodulin Into Phospholipid Vesicles," *J. Biol. Chem.* 262(5):2199-2205 (1987).

Gerson et al., "Severe Acquired Protein C Deficiency in Purpura Fulminans Associated with Disseminated Intravascular Coagulation: Treatment with Protein C Concentrate," *Pediatrics* 91(2):418-422 (1993).

Graham, et al., "A new technique for the assay of infectivity of human adenovirus 5 DNA.," *Virology.* 52(2):456-67 (1973).

Gregoriadis, "Liposomes," in *Drug Carriers in Biology and Medicine*, Chap. 14, pp. 287-341 (Academic Press, 1979).

Grey, et al., "Selective effects of protein C on activation of human monocytes by lipopolysaccharide, interferon-gamma, or PMA: modulation of effects on CD11b and CD14 but not CD25 or CD54 induction," *Transplant Proc.* 25(5):2913-4 (1993).

Grigoriev, et al., "A triple helix-forming oligonucleotide-intercalator conjugate acts as a transcriptional repressor via inhibition of NF kappa B binding to interleukin-2 receptor alpha-regulatory sequence," *J Biol Chem* 267(5):3389-95 (1992).

Grinell, et al., "Human protein C inhibits selectin-mediated cell adhesion: role of unique fucosylated oligosaccharide," *Glycobiology* 4(2):221-5 (1994).

Heaney, et al., "Membrane-associated and soluble granylocyte/macrophage-colony -stimulating factor receptor α submits are independently regulated in HL-60 cells," *Proc. Natl. Acad. Sci. U.S.A.* 92:2365-2369 (1995).

Heaney, ML and DW Golde, "Soluble cytokine receptors," *Blood* 87(3):847-857 (1996).

Hofsteenge, et al., "Effect of thrombomodulin on the kinetics of the interaction of thrombin with substrates and inhibitors," *Biochem. J.* 237:243-251 (1986).

Hogg, et al., "Identification of structural domains in protein C involved in its interaction with thrombin-thrombomodulin on the surface of endothelial cells," *J Biol Chem* 267(2):703-6 (1992).

Holt, et al., "An oligomer complementary to c-myc mRNA inhibits proliferation of HL-60 promyelocytic cells and induces differentiation," *Mol Cell Biol.* 8(2):963-73 (1988).

Horiuchi, et al., "Soluble interleukin-6 receptors released from T cell of granulocyte/macrophage cell lines and human peripheral blood mononuclear cells are generated through an alternative splicing mechanism," *Eur. J. Immunol.* 24:1945-1948 (1994).

Ishii and Majerus, "Thrombomodulin is Present in Human Plasma and Urine," *J. Clin. Invest.* 76:2178-2181 (1985).

Itakura, et al., "Synthesis and Use of Synthetic Oligonucleotides," in *Ann. Rev. Biochem.* 53:323-356 (1984).

Jackman, et al., "Human thrombomodulin gene is intron depleted: Nucleic acid sequences of the cDNA and gene predict protein structure and suggest sites of regulatory control," *Proc. Natl. Acad. Sci. (USA)* 84:6425-6429 (1987).

Jiang, et al., "Nucleocytoplasmic transport is enhanced concomitant with nuclear accumulation of epidermal growth factor (EGF) binding activity in both 3T3-1 and EGF receptor reconstituted NR-6 fibroblasts," *J. Cell Biol.* 110:559-568 (1990).

Kabat, et al., Sequences of Proteins of Immunological Interest, 4th Ed. (U.S. Dept. Health and Human Services, Bethesda, MD, 1987).

Kaisho, et al., "BST-1, a surface molecule of bone marrow stromal cell lines that facilitates pre-B-cell growth.," *Proc Natl Acad Sci U S A*. 91(12):5325-9 (1994).

Kapiotis, et al., "Interleukin-4 counteracts pryogen-induced downregulation of thrombomodulin in cultured human vascular endothelial cells," *Blood.* 78(2):410-5 (1991).

Kozak, et al., "Point mutations define a sequence flanking the AUG initiator codon that modulates translation by eukaryotic ribosomes," *Cell* 44(2):283-92 (1986).

Kurosawa, et al., "Identification of functional Endothelial Protein C Receptor in Human Plasma," *J. Clin. Invest.* 1000(2): 411-418 (1997).

Kyte, et al., "A simple method for displaying the hydropathic character of a protein," *J Mol Biol* 157(1):105-32 (1982).

Laemmli, "Cleavage of Structural Proteins During the Assembly of the Head of Bacteriophage T4," *Nature*, 227:680-685 (1970).

Laszik, et al., "The Human Protein C Receptor Is Present Primarily on Endothelium of Large Blood Vessels," *Circulation*, 96(10):1-9 (1997).

Le Bonniec, et al., "The role of calcium ions in factor X activation by thrombin E192Q," *J Biol Chem* 267(10):6970-6 (1992).

Ledbetter, et al., "Covalent association between human thymus leukemia-like antigens and CD8(Tp32) molecules," *J Immunol* 134(6):4250-4 (1985).

Lentz et al., "Regulation of Thrombomodulin by Tumor Necrosis Factor-β: Comparison of Transcriptional and Post-transcriptional Mechanisms," *Blood* 77(3):543-550, (1991).

Lewis, et al., "Automated site-directed drug design: the concept of spacer skeletons for primary structure generation, " *Proc. R. Soc. Lond.*, 236(1283):125-140 (1989).

Lewis, et al., "Automated site-directed drug design: the formation of molecular templates in primary structure generation," *Proc. R. Soc. Lond.*, 236(1283):141-162 (1989).

Lobie, et al. "Nuclear translocation and anchorage of the growth hormone receptor," *J. Biol. Chem.* 269:31735-31746 (1994).

Lu, et al., "The Active Site of the Thrombin-Thrombomodulin Complex—A Fluorescence Energy Transfer Measurement of its Distance Above the Membrane Surface," *J. Biol. Chem.* 264(22):12956-12962 (1989).

Lust, et al., "Isolation of An mRNA Encoding a Soluble Form of the Human Interleukin-6 Receptor," *Cytokine* 4(2):96-100 (1992).

Maciag, et al., "An endothelial cell growth factor from bovine hypothalamus: identification and partial characterization," *Proc Natl Acad Sci U S A*. 76(11):5674-8 (1979).

Maher, "Nuclear Translocation of fibroblast growth factor (FGF) receptors in response to FGF-2," *J. Cell Biol.* 134: 529-536 (1996).

Maher, et al., "Inhibition of DNA binding proteins by oligonucleotide-directed triple helix formation.," *Science* 245(4919):725-30 (1989).

Maruyama, et al., "Increased expression of thrombomodulin on the cultured human umbilical vein endothelial cells and mouse hemangioma cells by cyclic AMP," *Thromb Res.* 61(3):301-10 (1991).

Mather, et al., "The 2.8 Å Crystal Structure of Gla-Domain-less Activated Protein C," *EMBO J.* 15(24):6822-6831 (1996).

Mathews, "Structure of a Nonadecapeptide of the Fifth EGF Domain of Thrombomodulin Complexed with Thrombin," *Biochemistry* 33:13547-13552 (1994).

McKinlay, et al., "Rational Design of Antiviral Agents," *Annual Review of Pharmacology and Toxicology*, 29:111-122 (1989).

Merrifield, "Solid-Phase Peptide Synthesis. I. The Synthesis of a Tetrapeptide," *J. Am. Chem. Soc.* 85:2149-2154 (1964).

Mizushima, et al., "pEF-BOS, a powerful mammalian expression vector," *Nucleic Acids Res.* 18(17):5322 (1990).

Moore, et al., "Tumor Necrosis Factor Leads to the Internalization and Degradation of Thrombosis from the Surface of Bovine Aortic Endothelial Cells in Culture," *Blood* 73(1):159-165 (1989).

Müllberg, et al., "The Soluble Human IL-6 Receptor," *J. Immunol.* 152:4985-4986 (1994).

Mulligan, et al., "The basic science of gene therapy," *Science* 260(5110):926-32 (1993).

Narang, et al., "Chemical Synthesis of Deoxyoligonucleotides by the Modified Triester Method," in *Methods Enzymol.* 65:610-620 (1980).

Nawroth, et al., "Modulation of endothelial cell hemostatic properties by tumor necrosis factor," *J Exp Med.* 163(3): 740-5 (1986).

Offensperger, et al., "In Vivo inhibition of duck hepatitis B virus replication and gene expression by phosphorothioate modified antisense oligodeoxynucleotides," *EMBO J.* 12(3): 1257-1262 (1993).

Ohdama, et al., "Plasma Thrombomodulin in Wegener's Granulomatosis as an Indicator of Vascular Injuries," *Chest* 106:666-671 (1994).

Olsen, et al., "Ca2 + dependence of the interactions between protein C, thrombin, and the elastase fragment of thromobomodulin. Analysis by ultracentrifugation," *Biochemistry* 31(3):746-54 (1992).

Orson, et al., "Oligonucleotide inhibition of IL2R alpha mRNA transcription by promoter region collinear triplex formation in lymphocytes," *Nucleic Acids Res* 19(12):3435-41 (1991).

Owen, et al., "The Conversion of Prothrombin to Thrombin," *J. Biol. Chem.* 249(2):594-605 (1974).

Panja, et al., "CD1d is involved in T cell-intestinal epithelial cell interactions," *J Exp Med.* 178(3):1115-9 (1993).

Parkinson, et al., "Stable Expression of a Secretable Deletion Mutant of Recombinant Human Thrombomodulin in Mammalian Cells," *J. Biol. Chem.* 265(21):12602-12610 (1990).

Perry & Davies, *QSAR: Quantitative Structure-Activity Relationships in Drug Design* pp. 189-193 (Alan R. Liss, inc. 1989).

Porcelli, et al., "CD1b restricts the response of human CD4-8- T lymphocytes to a microbial antigen," *Nature.* 360(6404):593-7 (1992).

Postel, et al., "Evidence that a triplex-forming oligodeoxyribonucleotide binds to the c-myc promoter in HeLa cells, thereby reducing c-myc mRNA levels," *Proc Natl Acad Sci U S A.* 88(18):8227-31 (1991).

Proudfoot, et al., "3' non-coding region sequences in eukaryotic messenger RNA," *Nature* 263(5574):211-4 (1976).

Quehenberger, et al., "Increased Levels of Activated Factor VII and Decreased Plasma Protein S Activity and Circulating Thrombomodulin During Use of Oral Contraceptives," *Thromb. Haemost.* 76:729-734 (1996).

Regan, et al., "The endothelial cell protein C receptor. Inhibition of activated protein C anticoagulant function without modulation of reaction with proteinase inhibitors," *J. Biol. Chem.* 271, 17499-17503 (1996).

Reitsma, et al., "Protein C Deficiency: A Database of Mutations, 1995 Update," *Thromb. Haemost.* 73:876-879 (1995).

Rezaie, et al., "Communication: Protein C Inhibitor Is a Potent Inhibitor of the Thrombin-Thrombomodulin Complex," *J. Biol. Chem.* 270(43):25336-25339 (1995).

Ripka, "Computers Picture the Perfect Drug," *New Scientist*, 54-57 (Jun. 16, 1988).

Rollins, et al., "Inhibition of Homologous Complement by CD59 is Mediated by a Species-Selective Recognition Conferred Through Binding to C8 Within C5b-8 or C9 Within C5b-9," *J. Immunol.* 146(7):2345-22351 (1991).

Rothbarth, et al., "cDNA-derived molecular characteristics and antibodies to a new centrosome-associated and G2/M phase-prevalent protein," *J Cell Sci.* 104 ( Pt 1):19-30 (1993. ).

Rouvinen, et al., "Computer-Aided Drug Design," *Acta Pharmaceutica Fennica*, 97:159-166 (1988).

Sadler, et al., "Structure-Function Relationships of the Thrombin-Thrombomodulin Interaction," *Haemostasis* 23 (suppl 1):183-193 (1993).

Sarin, et al., "Inhibition of acquired immunodeficiency syndrome virus by oligodeoxynucleoside methylphosphonates," *Proc. Natl. Acad. Sci. USA* 85(20): 7448-7794 (1989).

Sebestyen, et al., "DNA vector chemistry: the covalent attachment of signal peptides to plasmid DNA," *Nature Biotechnology* 16, 80-85 (1998).

Seligsohn et al., "Homozygous Protein C Deficiency Manifested by Massive Venous Thrombosis in the Newborn, " *N. Engl. J. Med.* 310(9):559-562 (1984).

Shaw, et al., "Modified deoxyoligonucleotides stable to exonuclease degradation in serum," *Nucleic Acids Res.* 19(4):747-750 (1991).

Stearns, et al., "The Interaction of a $Ca^{2+}$ -dependent Monoclonal Antibody with the Protein C Activation Peptide Region," *J. Biol. Chem.* 263(2):826-832 (1988).

Stearns-Kurosawa, et al,. "The endothelial cell protein C receptor augments protein C activation by the thrombin-thrombomodulin complex," *Proc. Natl. Acad. Sci. (USA)* 93:10212-10216 (1996).

Stern, et al., "Cultured bovine aortic endothelial cells promote activated protein C-protein S-mediated inactivation of factor Va," *J Biol Chem* 261(2):713-8 (1986).

Suzuki, et al., "Structure and expression of human thrombomodulin, a thrombin receptor on endothelium acting as a cofactor for protein C activation," *EMBO J.* 6(7):1891-1897 (1987).

Szostak, "In Vitro genetics," *TIBS* 19:89-93 (1992).

Takahashi, et al., "Circulating Thrombomodulin As a Novel Endothelial Cell Marker: Comparison of Its Behavior with von Willbebrand Factor and Tissue Type Plasminogen Activator," *Am. J. Hematol.* 41:32-39 (1992).

Takahashi, et al., "Circulating Thrombomodulin in Thrombocytopenic Purpura," *Am. J. Hematol.* 38:174-177 (1991).

Takano, et al., "Plasma Thrombomodulin in Health and Diseases," *Blood.* 76(10):2024-2029 (1990).

Tanaka, et al., "Increased Thrombomodulin Values in Plasma of Diabetic Men with Microangiopathy," *Clin. Chem.* 37(2):269-272 (1991).

Taylor et al., "C4b-Binding Protein Exacerbates the Host Response to *Escherichia coli*," *Blood* 78(2):357-363 (1991).

Taylor et al., "Protein C Prevents the Coagulopathic and Lethal Effects of *Escherichia coli* Infusion in the Baboon," *J. Clin. Invest.* 79:918-925 (1987).

Von Heijne, "A New Method for Predicting Signal Sequence Cleavage Sites," *Nucleic Acids Res.* 14(11):4683-4690 (1986).

Wada, et al., "Plasma Thrombomodulin as a Marker of Vascular Disorders in Thrombotic Thrombocytopenic Purpura and Disseminated Intravascular Coagulation," *Am. J. Hematol.* 39:20-24 (1992).

Wen, et al., "Human Thrombomodulin: Complete cDNA Sequence and Chromosome Localization of the Gene," *Biochemistry* 26:4350-4357 (1987).

Wickstrom, et al., "Human promyelocytic leukemia HL-60 cell proliferation and c-myc protein expression are inhibited by an antisense pentadecadeoxynucleotide targeted against c-myc mRNA," *Proc Natl Acad Sci U S A.* 85(4):1028-32 (1988).

Williams, et al., The immunoglobulin superfamily—domains for cell surface recognition., *Annu Rev Immunol* 6:381-405 (1988).

Xie, et al., "Nuclear localization of p185neu tyrosine kinase and its association with transcriptional transactivation," *Biochem. Biophys. Res. Comm.* 203:1589-1598 (1994).

Ye, et al., "The Active Site of Thrombin is Altered Upon Binding to Thrombolmodulin—Two Distinct Structural Changes are Detected by Fluorescence, but only one Correlates with Protein C Activation," *J. Biol. Chem.* 266(34): 23016-23021 (1991).

Ye, et al., "The Fifth and Sixth Growth Factor-like Domains of Thrombomodulin Bind to the Anion-binding Exosite of Thrombin and Alter Its Specificity," *J. Biol. Chem.* 267(16): 11023-11028 (1992).

Young, et al., "Triple helix formation inhibits transcription elongation in vitro," *Proc Natl Acad Sci U S A.* 88(22): 10023-6 (1991).

Zamecnik, et al., "Inhibition of replication and expression of human T-cell lymphotropic virus type III in cultured cells by exogenous synthetic oligonucleotides complementary to viral RNA," *Proc Natl Acad Sci U S A.* 83(12):4143-6 (1986).

Zamecnik, et al., "Inhibition of Rous sarcoma virus replication and cell transformation by a specific oligodeoxynucleotide," *Proc Natl Acad Scie U S A*.75:280-284 (1978).

Zhu, et al., "Systemic gene expression after intravenous DNA delivery into adult mice," *Science* 261(5118):209-11 (1993).

\* cited by examiner

TARGETING OF MOLECULES TO LARGE VESSEL ENDOTHELIUM USING EPCR

The United States government has certain rights in this invention by virtue of National Heart, Lung and Blood Institute of the Institutes of Health grant No. P01 HL54804 to Charles T. Esmon.

BACKGROUND OF THE INVENTION

The present invention is generally in the area of targeting delivery of nucleotides and other molecules to large vessel endothelium using the endothelial cell protein C/activated protein C receptor ("EPCR").

Endothelial cells are a primary defense mechanism against cellular infiltration and thrombosis. Abnormal function of the endothelial cells contributes to myocardial infarction (MI), stroke and the development of atherosclerotic plaque. Atherosclerosis and most other vascular disease primarily occur in large vessels. In particular, large vessels are prone to a variety of diseases leading to atherosclerosis and thrombosis, resulting in heart attacks, strokes, deep vein thrombosis and pulmonary emboli. Gene therapy to modify the vascular lesions would be desirable.

Unfortunately, targeting endothelial cells non-specifically is often inadequate. Since more than 95% of endothelial cells are in the capillaries, arterioles and postcapillary venules, any therapy directed toward endothelial cells per se runs the risk of systemic complications. One must be confident that the gene expression is limited to the desired cells when using a gene therapy approach. However, no means for specifically targeting delivery to large vessel endothelium, in contrast to small vessel endothelium, or other types of tissues, are known.

It is therefore an object of the present invention to provide a means for specifically targeting delivery to large vessel endothelium.

It is a further object of the present invention to provide a means for delivering an agent to the endothelial cell nucleus of large vessels.

SUMMARY OF THE INVENTION

EPCR is located primarily on the surface of endothelial cells of large vessels. It translocates from the cell surface to the nucleus, and can be used to direct uptake by the cells of molecules that bind to EPCR and materials covalently coupled to the EPCR binding molecules. Molecules which bind to the EPCR, such as activated protein C ("APC"), but not protein C ("PC"), will be transported specifically to the nucleus of endothelial cells, especially those of the large vessels. Molecules which bind to the EPCR, such as PC, will direct molecules to endothelial cells, especially those of the large vessels. Molecules to be delivered can be nucleic acid, such as DNA, proteins such as transcription factors, diagnostic agents or other types of drugs. Conjugates of the materials to be administered can be formed by ionic or covalent coupling, for example, through direct conjugation of an anti-EPCR monoclonal antibody to a protein, including fusion proteins, or through the covalent attachment of a positively charged polymer such as polylysine to an anti-EPCR antibody, where the positively charged polymer binds nucleic acid or other negatively charged molecules by ionic charges. Steptavidin and biotin can also be used to conjugate molecules to the anti-EPCR antibody.

Examples demonstrate selective transport to the nucleus mediated by antibodies to EPCR, transport of proteins and genes bound to the antibodies to EPCR by charged polymers and steptavidin-biotin coupling, and transport selectively of APC, but not PC, to the nucleus of large vessel endothelial cells.

DETAILED DESCRIPTION OF THE INVENTION

I. Delivery System Targeted to Large Vessel Endothelium
  A. EPCR

The endothelial cell protein C receptor is ideally suited to target genes or other materials to the endothelial cell population of choice. The protein is expressed at the highest levels on endothelium of large vessels, particularly arteries and is at very low or undetectable levels in capillaries, as described by Laszik, et al., *Circulation* 96, 3633–3640 (1997) and PCT/US97/20364 "Endothelium Specific Expression Regulated by EPCR Control Elements" Oklahoma Medical Research Foundation. Protein C can be seen to be associated with vessels that express EPCR, but not with those that do not.

EPCR was cloned and characterized, as described in PCT/US95/09636 "*Cloning and Regulation of an Endothelial Cell Protein C/Activated Protein C Receptor*" by the Oklahoma Medical Research Foundation and U.S. Pat. No. 5,695,993 issued Dec. 9, 1997, to Oklahoma Medical Research Foundation. The protein consists of 238 amino acids, which includes a 15 amino acid signal sequence at the N-terminus, and a 23 amino acid transmembrane region which characterizes the receptor as a type 1 transmembrane protein. The protein binds with high affinity to both protein C and activated protein C (Kd=30 nM), which is a naturally occurring anticoagulant, and binding is calcium dependent. A vector encoding EPCR can be obtained from Invitrogen Corporation, 3985B Sorrento Valley Boulevard, San Diego, Calif. 92121.

The method used herein is preferably used with cells that naturally express EPCR, although it is understood that cells that are genetically engineered to express EPCR can also be targeted using agents which bind EPCR, to obtain uptake by the EPCR-expressing cells of material conjugated to the EPCR-binding molecules.

B. Agents which Bind to EPCR

Agents which selectively bind to EPCR can be used to deliver materials selectively to large vessel endothelial cells. Exemplary agents include PC, antibodies and antibody fragments which bind to EPCR, and certain other proteins, including fusion proteins, which include the Gla domain of PC. Selection of the agent can be used to target the molecule to be delivered to either the nucleus or to the cytoplasm of the large vessel endothelial cells. For example, APC directs uptake to the nucleus; PC results in uptake primarily within the cytoplasma and organelles therein.

Antibodies to EPCR, whether they block protein C binding or not, are transported to the nucleus. This is because EPCR translocates to the nucleus, not because of antibody dependent translocation. As described in the examples, polyacrylamide gel electropheresis in detergent ("SDS-PAGE") and autoradiography shows $^{125}I$ labeled monoclonal antibody ("Mab") deposition in the nucleus as detected in nuclear extracts of the HUVEC. Mab 1500 does not block protein C binding to EPCR whereas Mab 1494 does block this binding. Antibodies are found in the nuclear extract. Control antibodies to Thrombomodulin are not detected in the nuclear extract.

Antibodies which can be used to bind to EPCR include polyclonal and monoclonal antibodies, and fragments thereof, produced by enzymatic cleavage or expression of recombinant nucleic acid molecules encoding the fragments. Methods for making EPCR and antibodies to EPCR are described by Stearns-Kurosawa, et al., *J. Biol. Chem.* 271, 17499–17503 (1996). Antibodies can be obtained using standard techniques using EPCR, either isolated from natural or recombinant sources as the immunogen. The antibodies can be used as naturally produced, cleaved enzymatically to yield fragments, or expressed from recombinant genes. Monoclonal antibodies can also be generated using standard techniques.

Recombinant and humanized antibodies can also be made using standard techniques. For example, Pharmacia's (Pharmacia LKB Biotechnology, Sweden) "Recombinant Phage Antibody System" (RPAS), which generates a single-chain Fv fragment (ScFv) that incorporates the complete antigen-binding domain of the antibody can be used to make antibodies. In the RPAS, antibody variable heavy and light chain genes are separately amplified from the hybridoma mRNA and cloned into an expression vector. The heavy and light chain domains are co-expressed on the same polypeptide chain after joining with a short linker DNA which codes for a flexible peptide. This assembly generates a single-chain Fv fragment (ScFv) which incorporates the complete antigen-binding domain of the antibody. Murine ScFv molecules can be "humanized" to further reduce the immunogenic stimulus presented.

Methods for "humanizing" antibodies, or generating less immunogenic fragments of non-human antibodies, are well known. A humanized antibody is one in which only the antigen-recognized sites, or complementarity determining hypervariable regions (CDRs) are of non-human origin, whereas all framework regions (FR) of variable domains are products of human genes. These "humanized" antibodies present a lesser xenograft rejection stimulus when introduced to a human recipient. To accomplish humanization of a selected mouse monoclonal antibody, the CDR grafting method described by Daugherty, et al., *Nucl. Acids Res.,* 19: 2471–2476, 1991, can be used. Briefly, the variable region DNA of a selected animal recombinant anti-idiotypic ScFv is sequenced by the method of Clackson, T., et al., *Nature,* 352: 624–688, 1991, incorporated herein by reference. Using this sequence, animal CDRs are distinguished from animal framework regions (FR) based on locations of the CDRs in known sequences of animal variable genes. Kabat, H. A., et al.1, *Sequences of Proteins of Immunological Interest, 4th Ed.* (U.S. Dept. health and Human Services, Bethesda, Md., 1987). Once the animal CDRs and FR are identified, the CDRs are grafted onto human heavy chain variable region framework by the use of synthetic oligonucleotides and polymerase chain reaction (PCR) recombination. Codons for the animal heavy chain CRDs, as well as the available human heavy chain variable region framework, are built in four (each 100 bases long) oligonucleotides. Using PCR, a grafted DNA sequence of 400 bases is formed that encodes for the recombinant animal CDR/human heavy chain FR protection.

Other molecules which can be used include proteins such as activated protein C ("APC"), or other proteins which include the vitamin K specific Gla domain of protein C, to direct binding to EPCR. Activated protein C is targeted to the nucleus and hence can be used to carry other proteins or DNA into the nucleus. In contrast, protein C is internalized by the receptor, but the protein C is not targeted to the nucleus. Nevertheless, protein C could be modified with an expression vector and could serve as a means of delivering genes to large vessel endothelium. The genes could then be targeted to the nucleus by a variety of means including attachment of nuclear targeting amino acid peptide sequences to the DNA such as the SV40 nuclear targeting sequence, described by Sebestyén, et al., *Nature Biotechnology* 16, 80–85 (1998).

C. Molecules to be Delivered

A variety of materials can be delivered, ranging from nucleic acids to proteins to diagnostic agents to drugs. In the preferred embodiment, these materials will be directed to the nucleus, particularly in the case of molecules to be expressed.

Nucleic acid molecules include vectors for expression of a gene or cDNA encoding a particular protein, molecules which inhibit or alter expression of a particular endogenous nucleic acid molecule, such as an antisense molecule, triplex forming oligonucleotide, ribozyme or external guide sequence for a ribozyme.

Many different genes have been identified as candidates to minimize vascular defects including tissue plasminogen activator, agents to inhibit the expression of leukocyte adhesion molecules, thrombomodulin, nitric oxide synthase, etc. The delivery of proteins or protein expression inhibitors, directly or via gene therapy, specifically to large vessel endothelial cells, is one means for addressing these clinical conditions. For example, the anti-thrombotic potential of endothelium can be increased by delivering agents that prevent thrombosis, such as thrombomodulin, heparin proteoglycans, tissue factor pathway inhibitor (TFPI, a potent inhibitor of the tissue Factor—Factor VIIa-Factor X complex), etc. Fibrinolytic activity can be increased by overexpression of tissue plasminogen activator (tPA) or urokinase. Expression of adhesion molecules such as P-selectin or ICAMs can be inhibited to minimize or decrease leukotye infiltration. Transcription factors can be used to induce expression of particular proteins.

Diagnostic agents include molecules which can be used for diagnostic purposes, including radiolabels, fluorescent labels, enzymatic labels, and other materials.

Drugs include molecules which are not normally transported efficiently, or selectively, into endothelial cells, especially those of the large vessels. These may be antiinflammatories, anticoagulants, anti-cytokines, growth hormones, or of any other purpose for which transport into endothelial cells is desirable.

Immunoprecipitates of surface biotinylated EPCR shown as a function of time demonstrate that, since both the surface labeled EPCR and the antibody EPCR complex translocate to the nucleus, translocation is independent of the antibody and hence any agent that binds tightly to EPCR can be translocated to the nucleus. For instance, a luciferase reporter gene construct bound to polylysine modified anti-EPCR monoclonal antibodies can be transported to the nucleus as evidenced by the antibody dependent expression of luciferase, as shown by the examples. No expression occurs if the construct is added to antibody that has not been modified with polylysine.

D. Methods of Binding to EPCR

The molecules to be delivered must be coupled to the agents which bind to the EPCR. The molecules can be conjugated directly or indirectly to the agents which bind to the EPCR. Binding can be covalent or ionic. Direct binding can be obtained using standard chemical coupling techniques such as using succinic anhydride and published methodology or by expression of the agent and molecule as a fusion protein. Indirect binding can be obtained through an intermediate molecule, such as a positively charged polymer like lysine (which binds to negatively charged molecules such as DNA), steptavidin which binds to biotin, either of which can be conjugated to the agent binding the EPCR, or expressed as a fusion protein with the agent binding the EPCR, or through the use of a chimeric antibody which binds both the EPCR and the molecules to be delivered.

Examples of useful chimeric antibodies include antibodies which bind both EPCR and DNA and antibodies which bind to both EPCR and whatever other molecule is to be delivered. Chimeric antibodies can be made using standard techniques. For example, chimeric antibodies composed of one variable region of anti-DNA antibody can be fused to one variable region of anti-EPCR antibody. Preferably both antibodies are humanized to minimize the immune response.

An example of protein delivery to the nucleus of large vessel endothelial cells is shown in the examples. Streptavidin was carried into the nucleus on biotinylated anti-EPCR mAB, JRK 1500.

Agents binding to EPCR can be coupled to molecules such as polylysine, polypyrroles, chitosan and other molecules known to ionically bind to DNA or other negatively charged molecules to be delivered. These are typically polymers including numerous positively charged groups.

II. Methods for Administration

Translocation of cell surface receptors to the nucleus has previously been shown for other receptors, including the receptors for fibroblast growth factor (FGF) (Maher, P. A. *J. Cell Biol.* 134: 529–536 (1996)), epidermal growth factor (EGF) (Holt, et al., *Biochem. Pharmacol.* 47: 117–126 (1994; Xie, Y. and M.-C. Hung. *Biochem. Biophys. Res. Comm.* 203: 1589–1598 (1994)); insulin (Jiang, L.-W. and M. Schindler. *J. Cell Biol.* 110: 559–568 (1990)), interleukin 1 (Curtis, et al. *J. Immunol.* 144: 1295–1303 (1990)), growth hormone (Lobie, et al. *J. Biol. Chem.* 269: 31735–31746 (1994)). In all of these cases, translocation requires binding of the receptor ligand to the receptor. Many of these ligands have adverse biological effects causing cellular proliferation (FGF and EGF) or inflammation (IL-1) (Curtis, et al. 1990) and hence the agonist is inappropriate for general therapy.

As described herein, a delivery means has been developed which is restricted to large vessel endothelium and hence can serve to deliver genes, transcription factors or other cellular modifiers to the nucleus of the large vessel endothelium specifically where the major complications of many cardiovascular diseases are manifested primarily. In the case of EPCR nuclear translocation, serum stimulates the process, but is not required. This means that enhanced delivery may be obtained during inflammation or coagulation processes, which typically accompany the disorders to be treated, or are more pronounced in the areas of the patient where treatment is desired.

In the preferred embodiment, the conjugate of the agent binding to the EPCR and the molecule to be delivered is administered intravascularly to a patient for administration throughout the blood vessels of the body. In another embodiment, the conjugate is administered to a region of a body in need of treatment thereof, for example, during angioplasty. Alternatively, the material can be used in vitro, to treat isolated cells, which can remain in culture or be returned to a patient in need of treatment thereof. The number of molecules to be administered will be determined empirically, based on the efficiency of uptake, the condition to be treated, the number of cells to be treated, the severity of the condition, and other variables normally considered in determining an effective amount.

The conjugate will typically be administered in an appropriate pharmaceutically acceptable carrier such as phosphate buffered saline, saline, or other materials used for administration of drugs intravenously. Conjugate can be administered alone or in combination with other therapeutic agents, such as anticoagulants, antiinflammatories, vasoconstrictors or other drugs appropriate for treatment of the disease indication.

The conjugate can alternatively be administered in a carrier such as a polymeric gel if applied topically or locally, for example, during angioplasty, particularly if administered using the angioplastic catheter, or directly, during surgery. Such catheters and polymeric materials are known, for example, as described in U.S. Pat. No. 5,779,673 to Roth, et al., U.S. Pat. No. 5,749,968 to Melanson, et al., and U.S. Pat. No. 5,698,189 to Rowe, et al. See also WO 96/20732 by Chiron Viagene which discloses polymeric materials such as polybrene to enhance transfer of material into cells to be genetically engineered and WO 96/21470 by Genemedicine, Inc. which describes polymers such as the polyoxyethylene oxides (Pluronics™ and Polaxomers™ sold by BASF) to retain genetic material at a site for transduction, and to increase efficiency of transduction. Other carriers can also be used, such as microparticles which provide for controlled release.

The amount to be administered can be determined based on the in vivo half-life of the conjugate, the efficiency of uptake, and the area to be treated. Treatment can be repeated as necessary, based on clinical judgement, in view of patient response. A pharmaceutically effective amount is that which achieves a clinical response, depending on the disorder to be treated.

The present invention will be further understood by reference to the following non-limiting examples.

Experimental Procedures

Isolation of Nuclei and Nuclear Extracts

Cells in 100 mm culture dishes were rinsed three times with cold Hank's buffered salt solution, (HBSS), and suspended in 1.5 ml of cold cell lysis buffer (10 mM HEPES, pH 7.5, 10 mM KCl, 0.1 mM EDTA, 0.1 mM EGTA, 1 mM DTT, 0.5 mM PMSF) by gentle scraping with a rubber policeman. The cells were allowed to swell on ice for 15 min, then 93.8 $\mu$l of a 10% solution of NP-40 was added and the tube was vortexed vigorously for 10 sec. Nuclei were pelleted by centrifugation for 30 sec in a microfuge, and washed twice with cell lysis buffer containing 0.5% NP-40. The nuclear pellets were extracted by nuclear extraction buffer (0.1% NP-40, 20 mM HEPES, pH 7.5, 0.4 M NaCl, 1 mM EDTA, 1 mM EGTA, 1 mM DTT, 1 mM PMSF, 1

μg/ml leupeptin, 1 μg/ml aproptinin, 1 mM benzamidine) at 4° C. for 1 hr. Nuclear extracts were present in the supernatants after centrifugation at 4° C. for 15 min.

Translocation of EPCR from the Plasma Membrane to the Nucleus

Cells in 100 mm culture dishes were labeled for 10 min at RT with 0.5 mg/ml sulfo-NHS-LC-Biotin in HBSS with 1 mM $Mg^{2+}$ and $Ca^{2+}$, rinsed with HBSS1 M $Ca^{2+}$ and $Mg^{2+}$, and then cultured with fresh medium at 37° C. for the indicated time. The cells were rinsed with ice-cold HBSS, lysed and the nuclear extracts were prepared as described above. The cell lysates without nuclei and nuclear extracts were immunoprecipitated with an anti-EPCR mAb (JRK1496, a murine anti-human EPCR antibody which blocks PC/APC binding to EPCR) resin at 4° C. for 2 hr, and the immunoprecipitates were washed with 2 M NaCl, 20 mM Tris-HCl, pH 7.5 with 0.1% Lubrol™ PX twice and 0.15 M NaCl, 20 mM Tris-HCl, pH 7.5 with 0.1% Lubrol™ PX twice, eluted by boiling for 3 min in 50% ethylene glycol, 5 mM MES, pH 6.0, 0.1% Lubrol™ PX plus 1X Laemmli sample buffer. Samples were subjected to 10% SDS-PAGE. Western blots were performed using streptavidin conjugated horse radish peroxidase (HRP) and developed with ECL system (Amersham).

Immunofluorescence Microscopy

HUVECs were rinsed with HBSS (1 mM $Ca^{2+}$, $Mg^{2+}$), fixed for 5 min with 4% paraformaldehyde in HBSS, and permeabilized for 5 min with 0.05% saponin. Permeabilized cells were incubated with 1% BSA for 30 min and then incubated with a mAb anti-EPCR (JRK1501, a murine monoclonal antibody to human EPCR which blocks PC/APC binding to EPCR, 10 g/ml) and a rabbit pAb anti-caveolin (10 μg/ml) in HBSS for 30 min, rinsed with HBSS, stained with FITC-conjugated goat anti-rabbit IgG (10 μg/ml) and Cy3 conjugated goat anti-mouse IgG (10 μg/ml) in HBSS for 30 min, rinsed with HBSS. Slides were mounted with Slow FADE and sealed with nail polish. Dual labeled cells were examined with a laser scanning confocal microscope. (The Cy3 conjugated goat anti mouse IgG stained the nucleus and caucolae providing confirmation of nuclear localization.)

DNA-mAb Complex and Transfection 1.7 mg mAb anti-EPCR (JRK1500, an antibody that does not block protein C binding) in 1 ml 10 mM sodium phosphate buffer, pH 7.0 was mixed with 0.25 ml 0.1 M sodium periodate in the same buffer, incubated for 15 min at room temperature (RT). The reaction mixture was buffer exchanged with 1 mM sodium acetate buffer, pH 4.0 on a PD-10 column (Pharmacia), 1.5 ml periodate oxidized mAb (1.4 mg) was collected and mixed with 0.5 ml poly-L-lysine (3 mg, mol. wt.=20,000) in 20 mM sodium carbonate buffer, pH 9.5, and incubated for 2 hr at RT. Sodium borohydride (0.1 ml, 4 mg/ml) was added and the reaction mixture then incubated on ice water for 1 hr. Free poly-L-lysine was removed by four cycles of concentration and 10 fold dilution with 10 mM glycine, pH 4.2 using a Millipore BIOMAX-100K™ ultrafilter. The overall yield of mAb-poly-L-lysine conjugate was about 70%.

The DNA-mAb complex was made by mixing 0.625 μg pGL3 vector vector which contains the luciferase insert (Promega) in 50 μl 10 mM HEPES, pH 7.5, 150 mM NaCl (HBS) and 0.42 $OD_{280}$ mAb-poly-L-lysine conjugate in 50 μl HBS and incubating for 30 min at RT. EA.hy296 cells were cultured in 12 well plates in 50 μl 10 mM HEPES, pH 7.5, 150 mM NaCl (HBS) with 0.42 $OD_{280}$ mAb-poly-L-lysine conjugate in 50 μl HBS and incubating for 30 min at RT. EA.hy926 cells were cultured in 12 well plates in Dulbecco's minimal essential medium containing 10% supplemented calf serum to 70% confluency. The media was replaced with 0.9 ml fresh media and 100 μl of the DNA-mAb complex was then added.

EXAMPLE 1

Transport of Iodinated EPCR mAb into the Nucleus of Endothelial Cells

Human umbilical vein endothelial cells (HUVEC) were cultured with 30 nM $^{125}I$ labeled Fab of anti-EPCR mAb (JRK 1500) for 1 hr at 37° C. Approximately 10% of the cell associated anti-EPCR mAb was found in the nuclear extract (4,496 of the 43,944 cpm bound).

EXAMPLE 2

Transport of Biotyinylated EPCR mAb into the Nucleus Over Time

EPCR nuclear translocation was visualized, at 0, 0.5, 1, 2 and 3 hours. EA.hy926 cells were surface biotinylated and then cultured for the indicated time at 37° C. Cell lysates (excluding the nucleus) and nuclear extracts were immunoprecipitated by an anti-EPCR mAb resin. The immunoprecipitates were subjected to SDS-PAGE under reducing conditions and Western Blotting.

The results show that biotin-labelled EPCR was present in both the nuclear extracts as well as the cell lysates, excluding the nucleus. Maximum nuclear uptake occurred within 2 hrs.

EXAMPLE 3

Transfer of DNA Complexed with Poly-L-Lysine Conjugated with Anti-EPCR mAb

Figure 1:
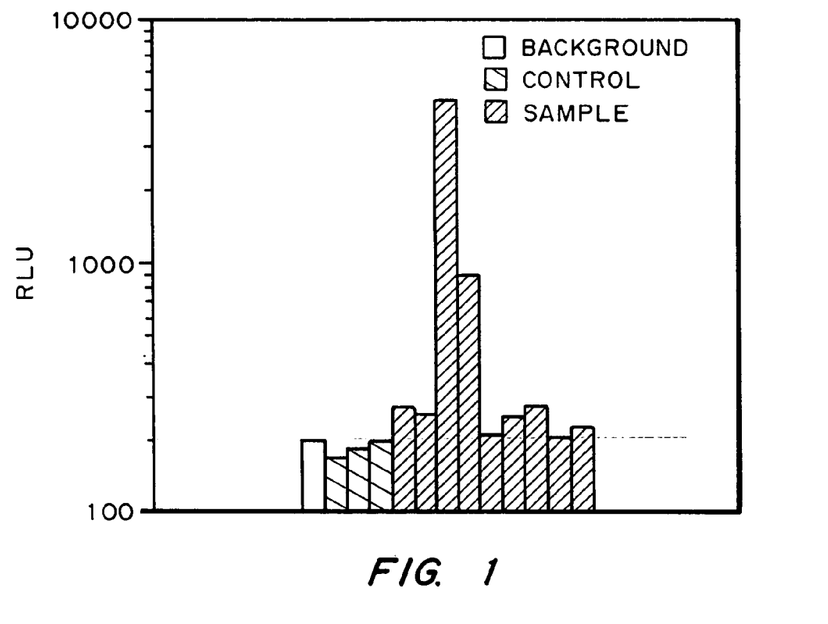
FIG. 1 is a graph of reporter gene transfer via a DNA anti-EPCR mAb-poly-L-lysine complex. Luciferase gene expression was measured in EA.hy926 cells transfected with the DNA-mAb conjugate as described in the experimental procedures. Control is the EA.hy926 cells transfected with same amounts of DNA, mAb and poly-L-lysine.

FIG. 1 is a graph of reporter gene transfer via a DNA anti-EPCR mAb-poly-L-lysine complex. Luciferase gene expression was measured in EA.hy926 cells transfected with the DNA-mAb conjugate as described in the experimental procedures. Control is the EA.hy926 transfected cells transfected with the same amounts of DNA, mAb and Poly-L-lysine but without polylysine conjugation.

The results demonstrate that there is much higher reporter gene transfer in the transfected cells, establishing that DNA can be transported into cell nuclei using a mAb to EPCR.

EXAMPLE 4

Figure 2:
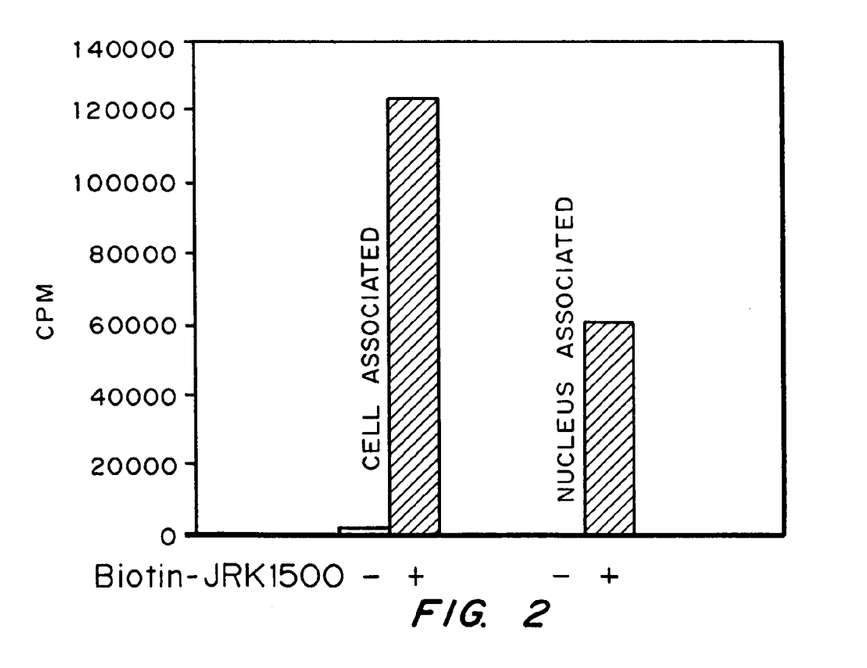
FIG. 2 is a graph of $^{125}I$ streptavidin nuclear delivery via biotinylated anti-EPCR mAb EA.hy926 cells cultured with 13.9 nM 125I labeled streptavidin in the absence (−) or presence (+) of 11.1 nM biotinylated anti-EPCR mAb (JRK1500) for 1 hr at 37° C.

Biotin Labeled EPCR mAb can be Used for Nuclear Delivery of Streptavidin Conjugated Moieties FIG. 2 is a graph of $^{125}I$ streptavidin nuclear delivery via biotinylated anti-EPCR mAb. EA.hy926 cells cultured with 13.9 nM 125I labeled streptavidin in the absence (−) or presence (+) of 11.1 nM biotinylated anti-EPCR mAb (JRK1500) for 1 hr at 37° C.

The results demonstrate that the streptavidin can be delivered to the nucleus.

EXAMPLE 5

Figure 3:
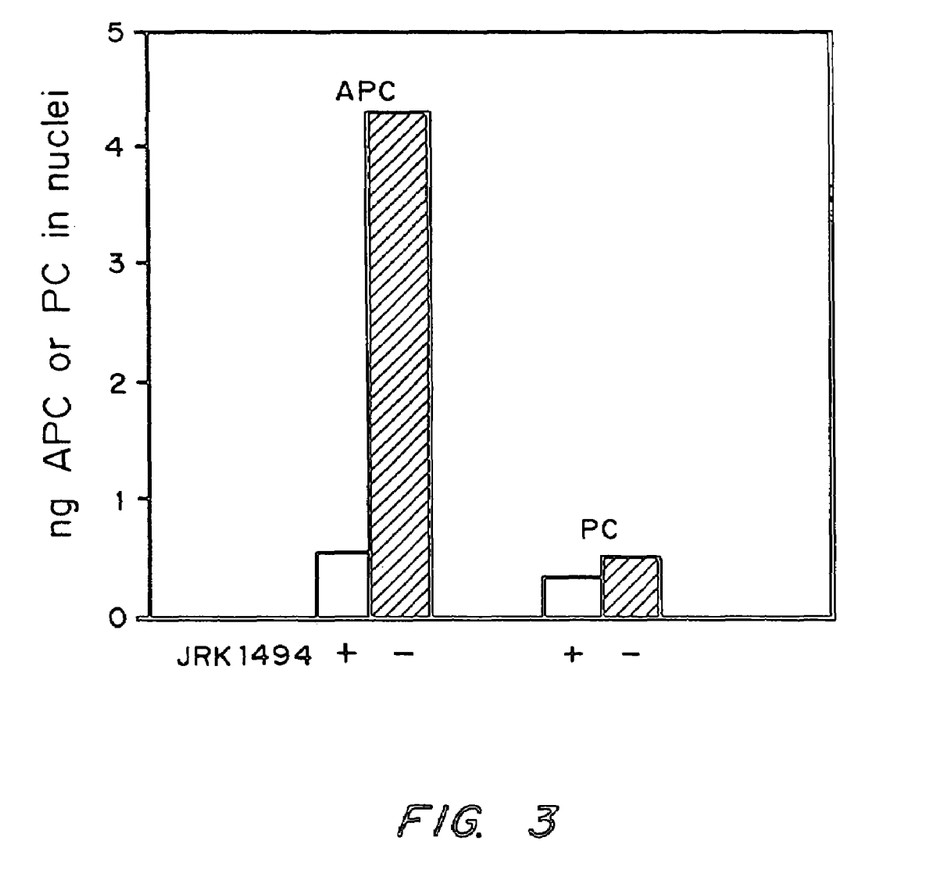
FIG. 3 is a graph of EPCR mediated nuclear translocation of APC, but not protein C, in human umbilical vascular endothelial cells ("HUVEC").

APC, But Not Protein C, is Transported to the Nucleus of Endothelial Cells by EPCR FIG. 3 is a graph of EPCR mediated nuclear translocation of APC, but not protein C, in HUVEC. HUVEC were incubated for 10 min at room temperature with or without 200 nM anti-EPCR mAB JRK 1494, an antibody that blocks protein C and binding and activity. The cells were then incubated with 30 nM $^{125}$I labeled APC or protein C for 1 hr at 37° C. Cells were washed with HBSS containing 0.5 mM EDTA to remove surface associated APC/protein C before the nuclei were isolated. The amounts of nuclear APC and protein C were calculated based on the specific activity of the labeled proteins.

In the case of APC, approximately 8% of the cell associated counts were in the nucleus. Neglible counts were associated with the nucleus when protein C was used.

EXAMPLE 6

Stimulation by Serum of EPCR Translocation

Serum stimulates EPCR nuclear translocation. EA.hy926 cells were surface biotinylated and then cultured in the absence or presence of bovine serum for 1 hr at 37° C. Cell lysate (excluding nucleus) and nuclear extracts were immunoprecipitated by an anti-EPCR mAb resin. The immunoprecipitates were subjected to SDA-PAGE under reducing conditions and Western Blotting.

The results show that a large portion of the biotin-labelled EPCR is transported into the nucleus. This means that clotting in an area could in some cases increase therapeutic gene/agent uptake.

Modifications and variations will be obvious to those skilled in the art and are intended to come within the scope of the appended claims.

We claim:

1. A method for selectively delivering a molecule to the nucleus of endothelial cells of large vessels, comprising
   directly administering a conjugate to large vessel endothelial cells,
   wherein the conjugate comprises an agent binding selectively to endothelial protein C receptor (EPCR) which causes uptake by the cell and transfer into the nucleus of the molecule to be delivered,
   wherein the conjugate is formed between the molecule to be delivered and an agent selected from the group consisting of activated protein C and an antibody to EPCR.

2. The method of claim 1 wherein the conjugate is formed between the molecule to be delivered and an antibody to EPCR.

3. The method of claim 1 wherein the conjugate is formed between the molecule to be delivered and activated protein C.

4. The method of claim 1 wherein the conjugate comprises a chimeric antibody binding to the molecule to be delivered and to EPCR.

5. The method of claim 1 wherein the molecule to be delivered is a nucleic acid molecule, wherein the nucleic acid molecule is a gene or cDNA under the control of a promoter expressed in the nucleus of an endothelial cell, wherein the nucleic acid molecule is delivered by directly contacting the endothelial cells of large vessels with the nucleic acid molecule conjugate or by catheterization to the endothelial cells.

6. The method of claim 5 wherein the nucleic acid molecule is selected from the group consisting of triplex forming oligonucleotides, ribozymes, guide sequences for ribozymes, and antisense.

7. The method of claim 1 wherein the molecule to be delivered is selected from the group consisting of drugs, proteins and diagnostic agents.

8. The method of claim 1 wherein the molecule to be delivered is a protein.

9. The method of claim 8 wherein the protein is a transcription factor.

10. The method of claim 1 wherein the molecule to be delivered is coupled to the agent which binds to EPCR by molecules selected from the group consisting of streptavidin and biotin, and molecules having multiple positive charges.

11. The method of claim 1 wherein the conjugate is administered to large vessel endothelial cells in culture or isolated from an individual.

12. The method of claim 1 wherein the conjugate is administered directly to an individual.

13. A conjugate comprising an agent binding selectively to endothelial protein C receptor (EPCR) selected from the group consisting of activated protein C and antibodies reactive with EPCR, and a nucleic acid molecule to be delivered to a large vessel endothelial cell, wherein the conjugate is a chemical conjugate, or conjugate formed by indirect binding by a positively charged polymer, chimeric antibody or streptavidin.

14. The conjugate of claim 13 wherein the conjugate is formed between the nucleic acid molecule to be delivered and activated protein C.

15. The conjugate of claim 13 wherein the molecule to be delivered is a nucleic acid molecule in combination for means for directly contacting the nucleic acid molecule conjugate directly with the endothelial cells of large vessels, wherein the means are for in vitro treatment of the cells or by catheterization to the endothelial cells.

16. The conjugate of claim 15 wherein the nucleic acid molecule is a gene or cDNA under the control of a promoter expressed in the nucleus of an endothelial cell.

17. The conjugate of claim 15 wherein the nucleic acid molecule is selected from the group consisting of triplex forming oligonucleotides, ribozymes, guide sequences for ribozymes, and antisense.

18. The conjugate of claim 13 comprising coupling means which binds the nucleic acid molecule to be delivered to the agent which binds EPCR.

19. The conjugate of claim 18 wherein the coupling means is a positively charged polymer or molecule.

20. The conjugate of claim 18 wherein the coupling means is streptavidin-biotin.

21. The conjugate of claim 13 comprising a chimeric antibody which binds to EPCR and to the nucleic acid molecule to be delivered.

* * * * *

UNITED STATES PATENT AND TRADEMARK OFFICE
CERTIFICATE OF CORRECTION

PATENT NO.   : 6,953,568 B1
DATED        : October 11, 2005
INVENTOR(S)  : Esmon and Xu It is certified that error appears in the above-identified patent and that said Letters Patent is hereby corrected as shown below:

Column 10,
Line 51, after "comprising", insert -- a --.

Signed and Sealed this

Eighteenth Day of April, 2006

JON W. DUDAS
*Director of the United States Patent and Trademark Office*